(12) United States Patent
Laske et al.

(10) Patent No.: US 7,191,009 B2
(45) Date of Patent: Mar. 13, 2007

(54) MEANS FOR INCREASING IMPLANTABLE MEDICAL DEVICE ELECTRODE SURFACE AREA

(75) Inventors: Timothy G. Laske, Shoreview, MN (US); Gonzalo Martinez, Mendota Heights, MN (US); Lea A. Nygren, Bloomington, MN (US)

(73) Assignee: Medtronic, Inc., Minneapolis, MN (US)

(*) Notice: Subject to any disclaimer, the term of this patent is extended or adjusted under 35 U.S.C. 154(b) by 239 days.

(21) Appl. No.: 10/914,303

(22) Filed: Aug. 9, 2004

(65) Prior Publication Data
US 2006/0030893 A1    Feb. 9, 2006

(51) Int. Cl.
*A61N 1/00* (2006.01)
(52) U.S. Cl. .................... 607/37; 607/36; 607/121; 607/122; 607/5; 607/4; 607/9
(58) Field of Classification Search .............. 607/5, 607/9, 36, 37, 121, 122, 4
See application file for complete search history.

(56) References Cited

U.S. PATENT DOCUMENTS

| | | | |
|---|---|---|---|
| 3,915,174 A | 10/1975 | Preston .................. 128/419 P |
| 4,142,532 A | 3/1979 | Ware ...................... 128/419 P |
| 4,152,540 A * | 5/1979 | Duncan et al. ...... 174/152 GM |
| 4,154,248 A | 5/1979 | Jones ...................... 128/419 P |
| 4,182,345 A | 1/1980 | Grose .................... 128/419 P |
| 4,226,244 A | 10/1980 | Coury et al. ............ 128/419 P |
| 4,248,437 A | 2/1981 | Lemberger et al. ........ 273/243 |
| 4,602,637 A | 7/1986 | Elmqvist et al. ........ 128/419 P |
| 4,934,366 A | 6/1990 | Truex et al. ............ 128/419 P |
| 5,133,353 A | 7/1992 | Hauser .................. 128/419 D |
| 5,476,496 A | 12/1995 | Strandberg et al. ......... 607/122 |
| 5,531,766 A | 7/1996 | Kroll et al. .................... 607/5 |
| 5,601,607 A | 2/1997 | Adams ........................... 607/5 |
| 5,643,328 A * | 7/1997 | Cooke et al. ................. 607/36 |
| 5,658,321 A | 8/1997 | Fayram et al. ................ 607/36 |
| 5,673,473 A | 10/1997 | Johnson et al. ............ 29/592.1 |
| 5,683,433 A * | 11/1997 | Carson ....................... 607/36 |
| 5,713,926 A * | 2/1998 | Hauser et al. .................. 607/5 |
| 5,906,634 A | 5/1999 | Flynn et al. ................... 607/37 |
| 5,913,881 A | 6/1999 | Benz et al. .................... 607/36 |
| 5,916,238 A | 6/1999 | Hauser et al. .................. 607/5 |
| 5,980,973 A | 11/1999 | Onyekaba et al. .......... 427/2.24 |
| 6,029,089 A | 2/2000 | Hawkins et al. .............. 607/37 |
| 6,157,860 A | 12/2000 | Hauser et al. .................. 607/9 |
| 6,265,466 B1 | 7/2001 | Glatkowski et al. ......... 523/137 |
| 6,280,462 B1 | 8/2001 | Hauser et al. .................. 607/5 |
| 6,295,474 B1 | 9/2001 | Munshi ...................... 607/121 |
| 6,505,073 B2 | 1/2003 | Gramse ....................... 607/37 |
| 2001/0002000 A1 | 5/2001 | Kumar et al. ............. 204/192.1 |
| 2003/0040780 A1 | 2/2003 | Haeg et al. ................... 607/36 |
| 2004/0093036 A1 | 5/2004 | Eckerdal et al. ............... 607/9 |

FOREIGN PATENT DOCUMENTS

EP    1 287 851 A1    3/2003

* cited by examiner

*Primary Examiner*—Robert E. Pezzuto
*Assistant Examiner*—Natasha Patel
(74) *Attorney, Agent, or Firm*—Carol F. Barry; Girma Wolde Michael

(57) ABSTRACT

A surface area of an IMD electrode is increased by forming a conductive layer over an external portion of a sidewall of an IMD connector header and electrically coupling the conductive layer of the connector header to a conductive mounting surface of a hermetically sealed IMD housing; wherein the conductive mounting surface is an extension of an external conductive surface of the IMD, which external conductive surface forms the IMD electrode that is increased in surface area by the conductive layer formed over the connector header.

34 Claims, 4 Drawing Sheets

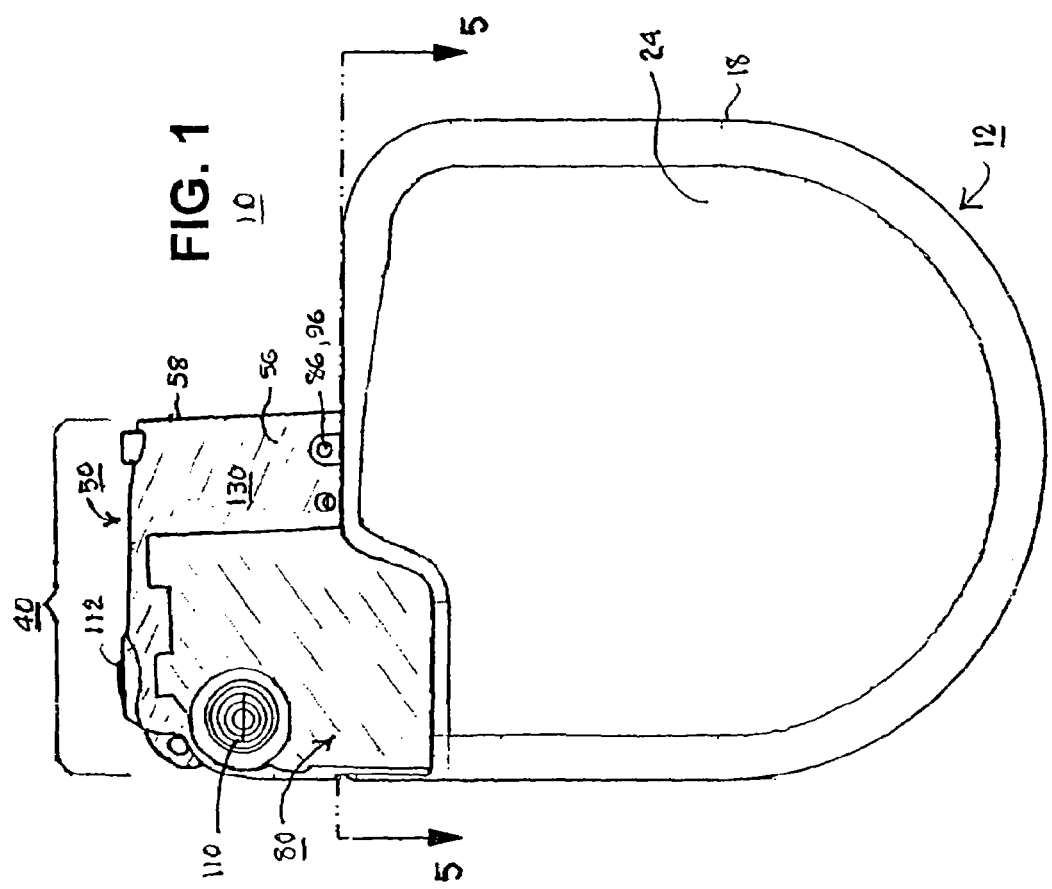
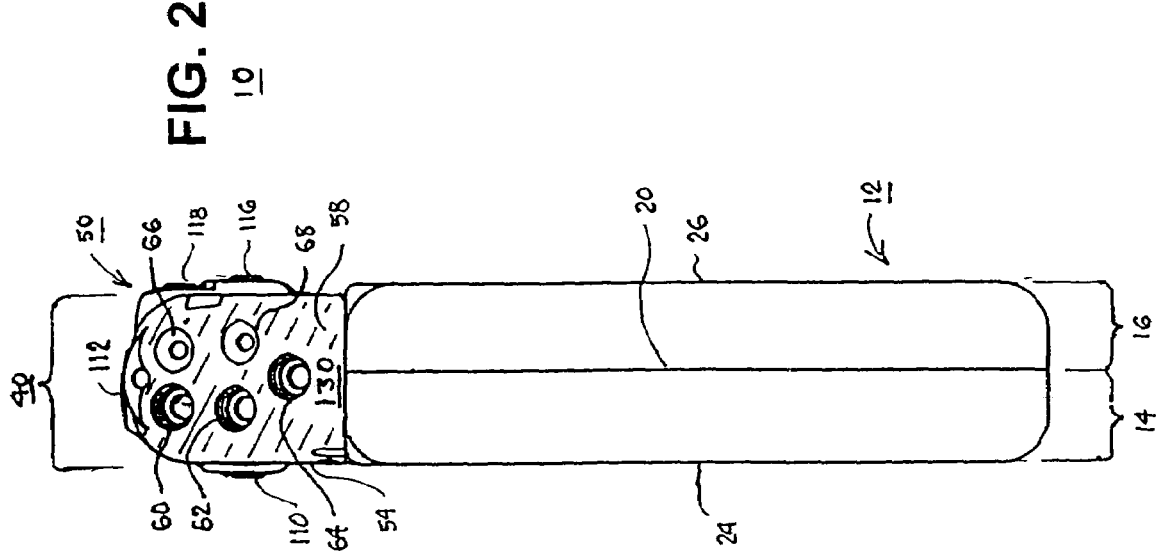

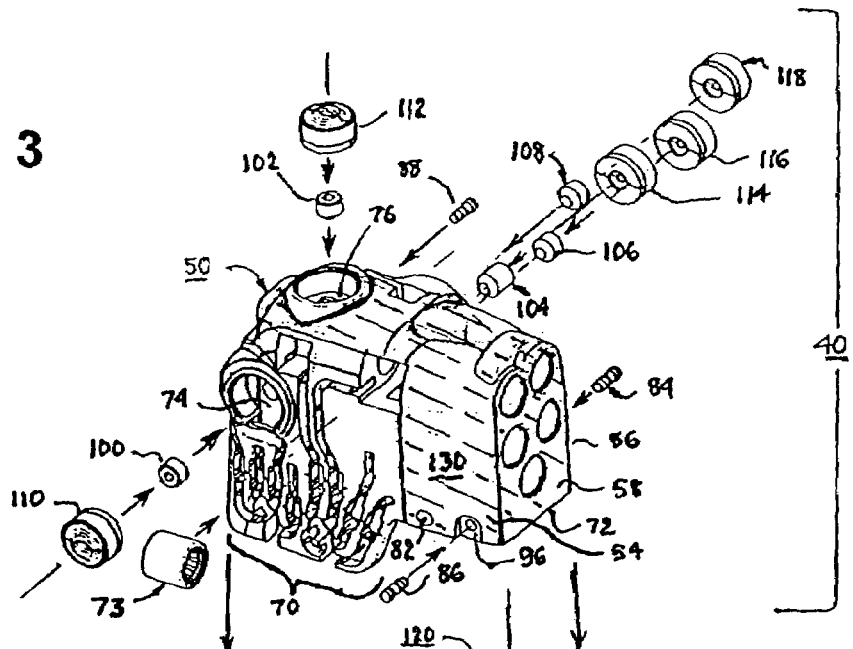
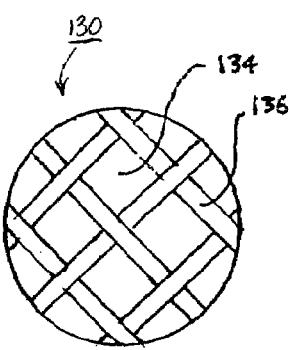
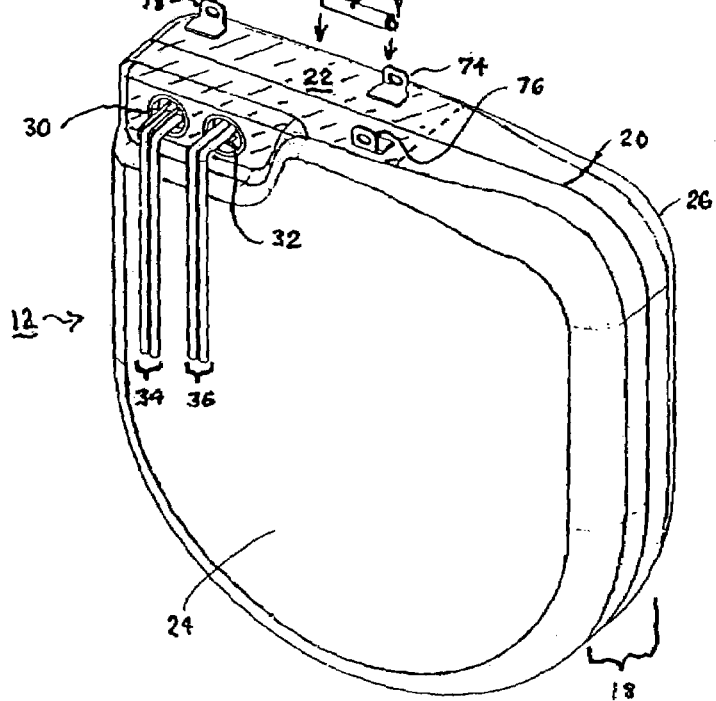
FIG. 3
FIG. 4

MEANS FOR INCREASING IMPLANTABLE MEDICAL DEVICE ELECTRODE SURFACE AREA

TECHNICAL FIELD

The present invention pertains to surfaces of implantable medical devices (IMD's) and more particularly to increasing an electrode surface area of an IMD.

BACKGROUND

At present, a wide variety of IMDs are commercially released or proposed for clinical implantation in the human body. Certain IMDs are manufactured as discrete units that may be selected by an implanting physician for a particular clinical use, being coupled, at implantation, with one or more medical electrical leads. Such an IMD may be an implantable pulse generator (IPG) or a physiologic monitor and particular examples include but are not limited to cardiac pacemakers, cardioverter/defibrillators, cochlear implants, muscle and nerve stimulators, and deep brain stimulators.

IMD's typically include signal processing and/or pulse generating circuitry powered by a battery and enclosed within a hermetically sealed enclosure or housing, sometimes referred to as a "can"; hermetically sealed housings are typically formed of a conductive biocompatible metal, commonly titanium, that is corrosion resistant when exposed to body fluids during chronic implant. A connector header attached to a header mounting surface of the can enables coupling of the IMD with one or more leads, whereby electrical connection is made between lead electrodes and the circuitry enclosed within the housing. The connector header includes a connector bore adapted to receive a lead connector terminal and formed in a body fabricated of a relatively hard, dielectric, non-conductive polymer, which encases and isolates header connector elements that are mounted within the connector bore. Each header connector element is connected by means of an insulated feed-through passing between the header and the interior of the can to the circuitry therein. Typically the connector header body is transparent so that an implanting physician can observe, upon inserting a lead connector terminal into the header connector bore, the seating of the lead connector terminal within the bore in order to verify electrical connection between connector elements of the lead connector terminal and corresponding header connector elements.

Typically, electrical medical leads support at least one stimulation and/or sensing electrode and certain IMD's employ all or part of an exterior conductive surface of the can as an electrode functioning in conjunction with one or more of the lead electrodes for delivering stimulation energy and/or sensing electrical body signals and/or for sensing impedance changes in tissue. For the delivery of cardiac pacing pulses, the can may act as an anode or indifferent electrode in conjunction with a lead cathode, and, for the delivery of monophasic or biphasic cardioversion/defibrillation shocks, the can may act as a high voltage electrode in conjunction with at least one other lead electrode of an opposite polarity. In the latter case, it is desirable that the can electrode surface area be maximized and that its electrical characteristics remain stable over the battery lifetime. It has been observed that the surface characteristics of titanium change over time when titanium is exposed to body fluids and when stimulation energy is delivered through it, for example by oxidation. Normally, delivery of pacing pulses over the lifetime of the battery does not alter the titanium surface characteristics enough to materially affect pacing and sensing functions or shorten battery life; however, it has been found that delivery of cardioversion/defibrillation shocks through the can electrode accelerates surface oxidation and passivation and may negatively affect sensing of both electrical signals and impedance and may reduce the efficiency of energy delivery, particularly cardioversion/defibrillation shocks, enough to shorten battery life. Impaired sensing and reduced efficiency of delivery of cardioversion/defibrillation shocks may also occur as the surface area of the can electrode is diminished. Over the years, the mass and volume of IMD's have been progressively reduced even as their function and longevity have increased. The goals of reducing IMD volume along with simplifying assembly have led to proposals to minimize the size of the connector header or to enclose it within the hermetically sealed can. A connector header enclosed within the can may make verification of a fully seated lead connector terminal within the connector bore difficult. Thus, a need remains for a means to augment an electrode surface area of an IMD without impairing the visual verification of lead connections within an IMD connector bore(s).

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIG. 1 is a side view of an exemplary IMD according to some embodiments of the present invention;

FIG. 2 is an end view of the IMD shown in FIG. 1;

FIG. 3 is an exploded perspective view of the IMD shown in FIGS. 1 and 2 according to an embodiment of the present invention;

FIG. 4 is an enlarged detail view of a conductive surface formed on a connector header according to one embodiment of the present invention;

DETAILED DESCRIPTION

Figure 5:
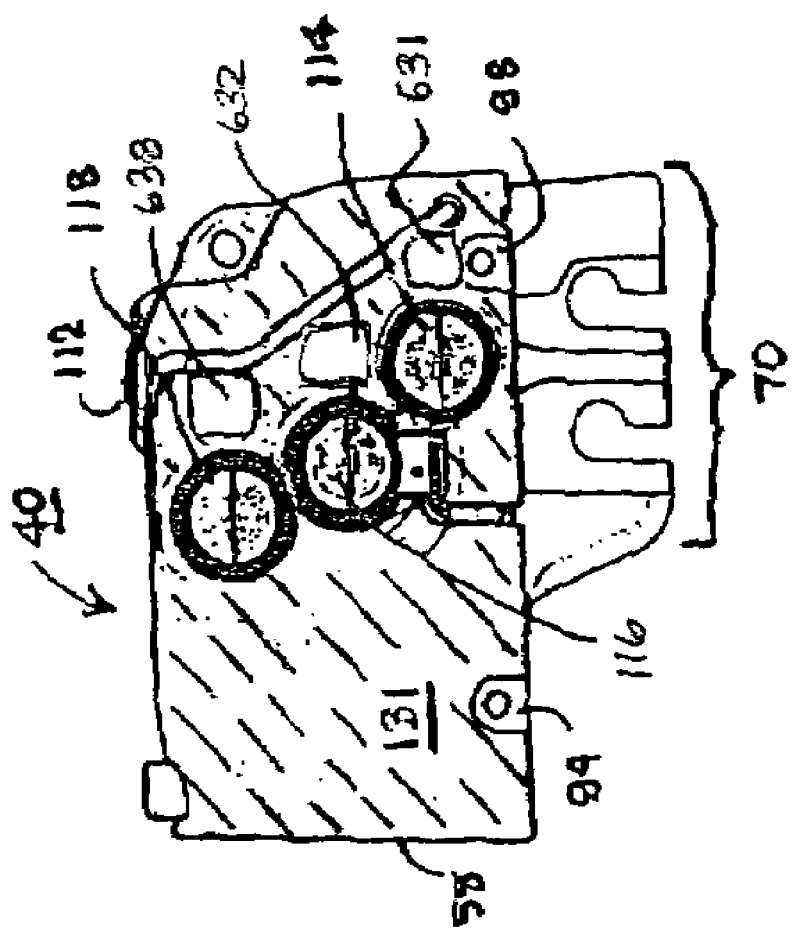
FIG. 5 is a side view of a connector header including a conductive surface according to another embodiment of the present invention.

In the following detailed description, references are made to illustrative embodiments of methods and apparatus for carrying out the invention. It is understood that other embodiments can be utilized without departing from the scope of the invention.

FIG. 1 is a side view of an exemplary IMD 10 according to some embodiments of the present invention; FIG. 2 is an end view of IMD 10; and FIG. 3 is an exploded perspective view of IMD 10. FIGS. 1 and 2 illustrate IMD 10 including a hermetically sealed can or housing 12 and a connector header 40 coupled thereto and including a body 50 and a fluid sealing and electrically insulating cover 80; connector header 40 is adapted to receive a number of medical electrical leads, each within a connector bore 60, 62, 64, 66 and 68, and a battery and electronic circuitry (not shown), enclosed within housing 12, would be capable of providing pacing and cardioversion/defibrillation therapies to be delivered via pace/sense and cardioversion/defibrillation electrodes carried by the leads. Examples of such IMD's are well known to those skilled in the art and a particular example is the Medtronic InSync™ Sentry™ Cardiac Resynchronization Therapy defibrillator, which also provides automatic fluid status monitoring, which can be programmed to alert patients and clinicians to changes in fluid accumulation in the lungs and thoracic cavity.

FIGS. 1 and 2 further illustrate housing 12 formed of can portions 14 and 16, for example made of titanium, laser welded together at weld seam 20; portions 14 and 16 each include a major side 24 and 26, respectively, which are supported and joined together at their side edges to form a mutual housing sidewall 18 having a sidewall width substantially defining a thickness of housing 12. Major sides 24 and 26 can be shaped having substantially circular, oval or rectilinear outlines and can have relatively straight and curved side edge sections; major sides 24 and 26 are typically planar and disposed substantially in parallel, although sides 24 and 26 may be bowed, convex or concave or otherwise contoured to some degree to conform to a particular implantation site. FIG. 3 illustrates a mounting surface 22, formed by a portion of sidewall 18 and a portion of major side 24, to which connector header 40 is fixedly mounted by means of mechanical post and pin connectors and medical adhesive, as will be further described below.

FIG. 3 further illustrates feedthroughs 30 and 32, which extend through a portion of mounting surface 22 that is formed along major side 24, and wire sets 34 and 36 extending therefrom, which would be routed through a set of channels 70 formed in connector header body 50, when header body 50 is mounted upon mounting surface 22; wire sets 34 and 36, having thus been routed and insulated from one another, couple connector elements within cavities of connector header body 5 to the circuitry enclosed within housing 12. The connector elements are disposed along lengths of connector bores 60, 62, 64, 66 and 68 and may take the form of spring contacts, for example a multi-beam spring contact 72 shown in FIG. 3, or setscrew connector assemblies, for example as illustrated by a block 74 and a corresponding setscrew 100, a block 76 and a corresponding setscrew 102, and setscrews 104, 106 and 108, whose corresponding blocks are not seen; such connector elements and their incorporation within connector bores of connector headers for the coupling of medical electrical leads are known to those skilled in the art. According to connector headers known in the art, setscrew assemblies are typically positioned for lead connector terminal pin connection in proximity to an end of each bore; in this case, setscrew block 74 is mounted in bore 62, setscrew block 76 in bore 60, the block corresponding with setscrew 108 in bore 66, the block corresponding to setscrew 106 in bore 68, and the block corresponding to setscrew 104 in bore 64; each of bores 62, 60, 66, 68 and 64 extends beyond the blocks to provide space for a lead connector pin to also extend beyond the blocks so that visual confirmation of full insertion is allowed.

Header body 50, including bores 60, 62, 64, 66 and 68, would typically be molded of a relatively stable and substantially optically transparent thermoplastic material, one example of which is TECOTHANE® urethane sold by Upjohn, Inc. Cover 80 (FIG. 1) is fitted over channels 70 and secured to body 50 following attachment of body 50 to housing 12, or cover 80 may simply be formed by a layer of cured medical adhesive. Furthermore, as illustrated in FIGS. 1–3, grommets 110, 112, 118, 116 and 114 are bonded to exterior surfaces of body 50 to seal setscrew assemblies while allowing passage of a torque wrench to tighten and loosen setscrews 100, 102, 108, 106 and 104, respectively.

According to the embodiment illustrated in FIG. 3, fixation of the header body 50 to the housing 12 is accomplished by a pin and post attachment mechanism: posts 74, 76 and 78 are shown extending away from the can mounting surface 22 in order to mate with slots 94, 96 and 98 of header body 50 (further shown in FIG. 5) when a header mounting surface 72 (FIG. 5) is brought to bear against mounting surface 22; pins 84, 86 and 88 would be fitted into side bores of slots 94, 96 and 98 aligned with bores of respective posts 74, 76 and 78 to secure header body 50 on mounting surface 22.

According to embodiments of the present invention, an outer surface of housing 12 is electrically conductive to be used as an IMD electrode and, to augment electrode surface area IMD 10, an electrically conductive layer 130 is formed over an exterior surface of header body 50 as illustrated in FIGS. 1–3; various embodiments of conductive layer 130 allow one to see into connector bores 60, 62, 64, 66 and 68 as lead connectors are being inserted therein to confirm full insertion of the lead connectors.

According to a first set of embodiments illustrated by FIGS. 1–3, conductive layer 130 is formed of a continuous optically transparent conductive material which has been applied to header body 50 and extends over outer header side walls 54, 56 and 58 and over at least a portion of header mounting surface 72; inwardly extending surfaces, for example those of bores 60, 62, 64, 66, and 68, other exposed cavities, and channels 70 could be masked during a coating process to apply layer 130. An example of a conductive transparent coating which may form layer 130 is a diamond-like-carbon film (DLC), which is superior in wear resistance, electrical insulation, and water repellency, has such a feature that a thickness thereof may be adjusted to provide good adhesion, and can be easily formed at a relatively low temperature by employing a plasma CVD method or the like. A DLC film can be rendered conductive by doping with boron during the gas phase deposition. Another example of a conductive transparent coating, which may be used for embodiments of the present invention, is one formed by Nanoshield™ technology developed by Eikos, Inc. and described in "Carbon Nanotube Based Transparent Conductive Coatings" authored by Paul J. Glatkowski, found at www.eikos.com/articles/conductive_coatings.pdf, and incorporated by reference herein.

According to a second set of embodiments, as illustrated in an enlarged detail view of FIG. 4, a cage or mesh formed by a biocompatible, corrosion resistant material, for example platinum, titanium, tantalum or gold forms conductive layer 130. The embodiment illustrated in FIG. 4 is formed of conductive bands 136, which are either wires formed about, or deposited as a coating over portions of the exterior surface of header body 50, including sidewalls 54 and 56 and at least a portion of the header mounting surface 72, leaving mesh windows 134 that enable viewing through sidewalls 54 and 56. If bands 136 have significant thickness, transparent silicone rubber medical adhesive may be applied between bands 136, filling in windows 134, to provide a relatively smooth exterior surface.

Figure 6:
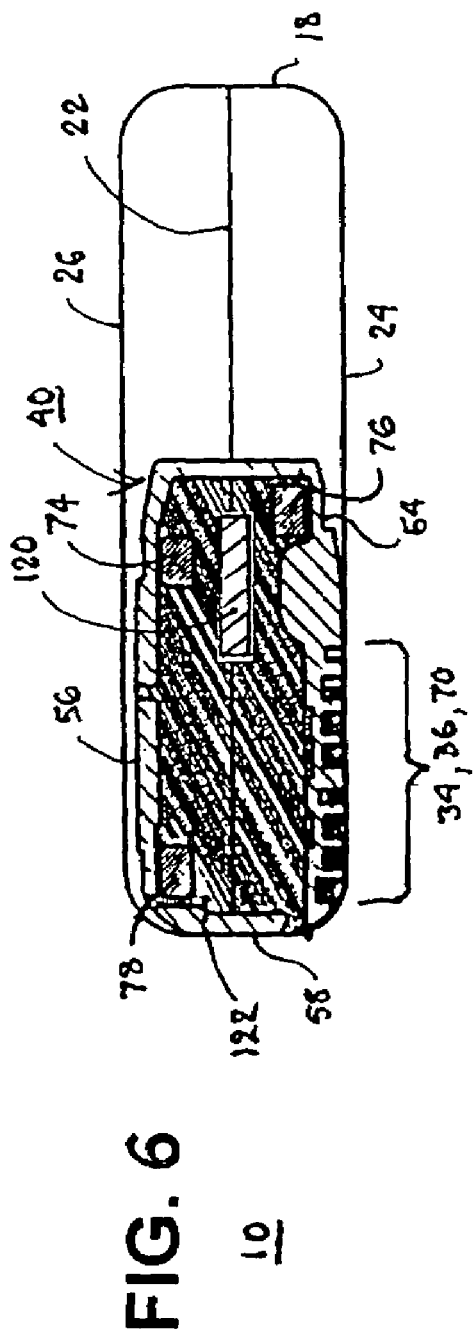
FIG. 6 is a section view through section line 5—5 of FIG. 1.

FIG. 6 is a side view of a connector header including a conductive surface according to yet another embodiment of the present invention. FIG. 6 illustrates a conductive layer 131 formed of an opaque conductive material and including windows 631, 632 and 633 positioned to provide viewing into bores 64, 68 and 66 (FIG. 2), beyond their associated setscrew blocks (previously described in conjunction with FIG. 3); likewise, windows would be provided for viewing into bores 60 and 62. Examples of materials that may be used for layer 131 include noble, refractory, metals and related alloys or oxides of a noble metal, particularly of the platinum group, including platinum, titanium, tantalum, gold, niobium, ruthenium, and of other high corrosion resistant materials, e.g., MP 35N, nickel-cobalt alloys. As with the mesh embodiment depicted in FIG. 4, if a thickness of layer 131 is significant, windows may be filled with a transparent silicone rubber medical adhesive to provide a relatively smooth exterior surface.

Figure 7:
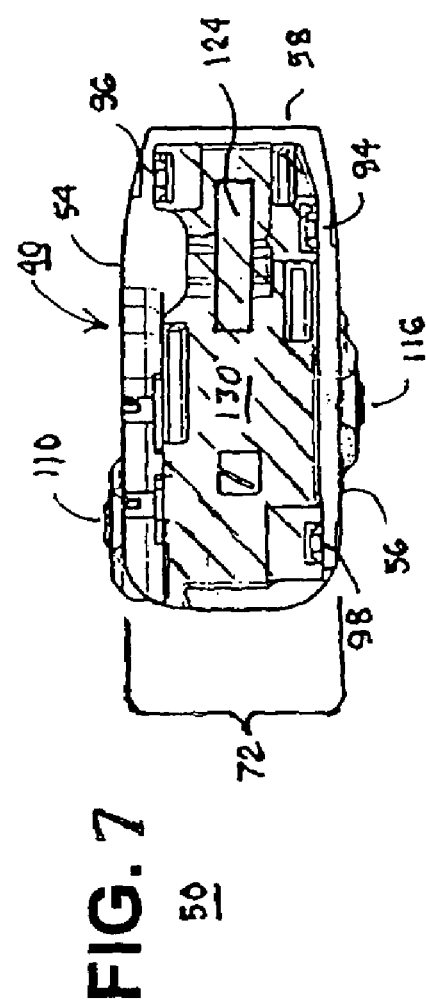
FIG. 7 is a bottom view of the connector header shown in FIG. 3.

In accordance with another aspect of the invention illustrated in FIGS. 3, 6 and 7, a conduction element 120, is interposed between mating mounting surfaces 22 and 72; upon assembly, conduction element 120 would be compressed to provide a robust electrical connection between the housing 12 and the header electrode 130 when mounting surfaces 22 and 72 are brought together and attached using the post and pin components previously described. According to the embodiment illustrated in FIG. 7, conduction element 120 is received in a shallow recess 124 of header mounting surface 72. According to the embodiment illustrated by FIG. 6, a silicone rubber seal 122 is formed, for example from a liquid silicone rubber medical adhesive, to surround the interface between mounting surface 22 and conduction element 120, isolating the connection therebetween from body fluids, and to fill a gap between the mating mounting surfaces 22 and 72; a fill port 82, illustrated in FIG. 3 may be incorporated to facilitate the application of rubber seal 122 after surfaces 22 and 72 are brought together. In addition, silicone rubber may be applied into a seam at the peripheries of the mounting surfaces 22 and 72. According to one embodiment, conduction element 120 is formed of an electrically conductive paste or epoxy or tape including adhesive properties. More than one conduction element 120 may be deposited between header mounting surface 72 and housing mounting surface 22 to provide redundant electrical connections.

Thus, exemplary methods and embodiments are described for incorporating at least a portion of the exterior surface area of the connector header of an IMD as a stimulation and/or sense electrode that does not interfere with visual confirmation of lead connector seating in a connector bore. In the foregoing detailed description, the invention has been described with reference to specific embodiments. However, it may be appreciated that various modifications and changes can be made without departing from the scope of the invention as set forth in the appended claims.

What is claimed is:

1. An implantable medical device (IMD) including a connector header, the connector header comprising:
   a header body formed of a non-conductive, optically transparent polymer and including a sidewall;
   at least one connector bore extending within the header body approximately parallel with the sidewall and including at least one connector element mounted therein; and
   a conductive layer comprising a conductive material formed on an external portion of the header body sidewall over a majority of the header body sidewall as an electrode surface, the conductive material being adapted to allow viewing through the sidewall into the connector bore;
   wherein the connector bore is adapted to receive a connector terminal of a medical electrical lead and the connector element is adapted to electrically couple the lead connector terminal to the IMD.

2. The IMD of claim 1, wherein the conductive material comprises an optically transparent conductive material.

3. The IMD of claim 1, wherein the conductive material comprises a mesh formed of conductive bands leaving mesh windows.

4. The IMD of claim 3, further comprising an optically transparent material filling the mesh windows.

5. The IMD of claim 1, wherein the conductive layer includes a window formed through the conductive material in proximity to an end of the bore beyond the connector element.

6. The IMD of claim 5, further comprising an optically transparent material filling the window.

7. The IMD of claim 1, wherein the connector element includes a setscrew.

8. The IMD of claim 1, wherein the connector element includes a spring contact.

9. An IMD, comprising:
   a hermetically sealed housing including a conductive external surface and containing electronic circuitry;
   conductors extending from the electronic circuitry through the housing and being isolated from the housing; and
   a connector header, through which the conductors are routed, mounted on the housing and including a header body having a sidewall formed of a non-conductive, optically transparent polymer, at least one connector bore extending within the header body approximately parallel with the sidewall, at least one connector element mounted within the connector bore and coupled to at least one of the conductors, and a conductive layer comprising a conductive material formed on an external portion of the header body sidewall over a majority of the header body sidewall as an electrode surface, the conductive material being adapted to allow viewing through the sidewall into the connector bore;
   wherein the connector bore is adapted to receive a connector terminal of a medical electrical lead and the connector element is adapted to electrically couple the lead connector terminal to the IMD.

10. The IMD of claim 9, wherein the conductive material comprises an optically transparent conductive material.

11. The IMD of claim 9, wherein the conductive material comprises a mesh formed of conductive bands leaving mesh windows.

12. The IMD of claim 11, further comprising an optically transparent material filling the mesh windows.

13. The IMD of claim 9, wherein the conductive layer includes a window formed through the conductive material in proximity to an end of the bore beyond the connector element.

14. The IMD of claim 13, further comprising an optically transparent material filling the window.

15. The IMD of claim 9, wherein the connector element includes a setscrew.

16. The IMD of claim 9, wherein the connector element includes a spring contact.

17. The IMD of claim 9, further comprising a conduction element disposed between the connector header and the housing to electrically couple the conductive layer of the connector header to the conductive external surface of the housing.

18. The IMD of claim 17, wherein the conductive element includes adhesive properties.

19. The IMD of claim 17, further comprising a fluid tight seal surrounding the conductive element.

20. A connector header for an IMD, comprising:
a header body formed of a non-conductive, optically transparent polymer and including a sidewall;
at least one connector bore extending within the header body approximately parallel with the sidewall and including at least one connector element mounted therein; and
a conductive layer comprising a conductive material formed on an external portion of the header body sidewall over a majority of the header body sidewall as an electrode surface, the conductive material being adapted to allow viewing through the sidewall into the connector bore;
wherein the connector bore is adapted to receive a connector terminal of a medical electrical lead and the connector element is adapted to electrically couple the lead connector terminal to the IMD.

21. The IMD of claim 20, wherein the conductive material comprises an optically transparent conductive material.

22. The IMD of claim 20, wherein the conductive material comprises a mesh formed of conductive bands leaving mesh windows.

23. The IMD of claim 22, further comprising an optically transparent material filling the mesh windows.

24. The IMD of claim 20, wherein the conductive layer includes a window formed through the conductive material in proximity to an end of the bore beyond the connector element.

25. The IMD of claim 24, further comprising an optically transparent material filling the window.

26. The IMD of claim 20, wherein the connector element includes a setscrew.

27. The IMD of claim 20, wherein the connector element includes a spring contact.

28. A method of increasing a surface area of an IMD electrode, the method comprising the steps of:
forming a conductive layer comprising a conductive material extending over an external portion of a sidewall an IMD connector header sidewall over a majority of the header body sidewall the header formed of a non-conductive optically transparent polymer;
electrically coupling the conductive layer of the connector header to a conductive mounting surface of a hermetically sealed IMD housing, the conductive mounting surface being an extension of an external conductive surface of the IMD, which external conductive surface forms the IMD electrode that is increased in surface area by the conductive layer formed over the connector header.

29. The method of claim 28, further comprising the steps of:
coupling a conduction element to the conductive layer of the connector header; and
positioning the conduction element on a mounting surface of the connector header to interface with the conductive mounting surface of the housing for electrical coupling of the conductive layer with the external conductive surface of the housing.

30. The method of claim 29, further comprising the step of forming a fluid tight seal about the conduction element-to-conductive mounting surface interface.

31. The method of claim 29, wherein the conduction element includes adhesive properties.

32. The method of claim 28, wherein forming the conductive layer includes leaving a window formed through the conductive material to facilitate viewing through the sidewall.

33. The method of claim 28, wherein the conductive material comprises an optically transparent conductive material.

34. An implantable medical device (IMD), comprising:
a hermetically sealed housing including a conductive external surface;
a header body formed of a non-conductive, optically transparent polymer and including a sidewall and a mounting surface, the header body being mounted on the housing along the mounting surface;
at least one connector bore extending within the header body approximately parallel with the sidewall, the connector bore being adapted to receive a connector terminal of a medical electrical lead and including at least one connector element mounted therein;
a conductive layer comprising a conductive material formed on an external portion of the header body sidewall over a majority of the header body sidewall as an electrode surface, the conductive material being adapted to allow viewing through the sidewall into the connector bore and further extending over a portion of the mounting surface; and
a conduction element disposed between the conductive material extending over a portion of the mounting surface and the housing for electrically coupling the conductive layer to the conductive external surface of the housing.

* * * * *